(12) United States Patent
Elze et al.

(10) Patent No.: US 8,161,818 B2
(45) Date of Patent: Apr. 24, 2012

(54) DEVICE FOR DETECTING A FLAW IN A COMPONENT

(75) Inventors: Stefan Elze, Bermen (DE); Rudolf Henrich, Ganderkesee (DE); Wilfried Pieles, Delmenhorst (DE); Ingrid Pieles, legal representative, Delmenhorst (DE)

(73) Assignee: Airbus Operations GmbH, Hamburg (DE)

( * ) Notice: Subject to any disclaimer, the term of this patent is extended or adjusted under 35 U.S.C. 154(b) by 361 days.

(21) Appl. No.: 12/606,466

(22) Filed: Oct. 27, 2009

(65) Prior Publication Data

US 2010/0107768 A1 May 6, 2010

Related U.S. Application Data

(60) Provisional application No. 61/109,345, filed on Oct. 29, 2008.

(51) Int. Cl.
*G01N 29/04* (2006.01)
(52) U.S. Cl. .............. 73/627; 73/596; 73/634; 73/644
(58) Field of Classification Search .............. 73/627, 73/596, 618, 620, 622, 629, 632, 633, 634, 73/644
See application file for complete search history.

(56) References Cited

U.S. PATENT DOCUMENTS

| | | | |
|---|---|---|---|
| 2,799,157 A | 7/1957 | Pohlman | |
| 4,557,145 A | 12/1985 | Perdijon | |
| 4,885,459 A * | 12/1989 | Norsworthy | 235/495 |
| 5,642,198 A * | 6/1997 | Long | 356/430 |
| 6,065,343 A * | 5/2000 | Kiuchi et al. | 73/622 |
| 6,092,420 A * | 7/2000 | Kimura et al. | 73/620 |
| 6,347,550 B1 * | 2/2002 | Kroening et al. | 73/598 |
| 7,021,143 B2 * | 4/2006 | Dasch | 73/620 |
| 7,278,969 B2 * | 10/2007 | Ueda | 600/463 |
| 2005/0126293 A1 | 6/2005 | Dasch | |
| 2009/0217763 A1 * | 9/2009 | Yamano | 73/622 |
| 2009/0301202 A1 * | 12/2009 | Bisiaux et al. | 73/622 |
| 2010/0005846 A1 * | 1/2010 | Yamano | 72/31.13 |
| 2011/0088476 A1 * | 4/2011 | Yamano et al. | 73/632 |

FOREIGN PATENT DOCUMENTS

| | | |
|---|---|---|
| CH | 318220 A | 4/1953 |
| DE | 10 2004 059441 A1 | 7/2005 |
| EP | 99816 A1 | 2/1984 |
| EP | 486689 A1 | 5/1992 |
| JP | 403225274 * | 10/1991 |
| WO | WO 2005/045598 A2 | 5/2005 |

OTHER PUBLICATIONS

German Office Action from DE 10 2008 043 293.8-52 dated May 8, 2009.

* cited by examiner

*Primary Examiner* — J M Saint Surin
(74) *Attorney, Agent, or Firm* — Jenkins, Wilson, Taylor & Hunt, P.A.

(57) ABSTRACT

The invention relates to a device for detecting a flaw in a fibre-reinforced component, in particular delamination in a bearing region of a hole, by means of at least one probe, wherein an ultrasound field is emittable and detectable by means of the at least one probe. The ultrasound field is coupled according to the invention to the component at an angle of incidence α of greater than 0° from a normal of an upper side of a component. The oblique radiation enables a higher degree of resolution to be achieved when detecting delamination in the bearing region of holes. Further variants of the device operate using at least one linear probe received in a self-positioning holder. The rotating linear probe is composed of a plurality of individual vibrator elements which are arranged at regular intervals behind one another.

11 Claims, 5 Drawing Sheets

VC sector B-scope display

FIG 9

Intermediate echo C-scope display    Back-wall echo C-scope display

FIG 10

VC sector B-scope display

FIG 11

Intermediate echo C-scope display

Back-wall echo C-scope display

DEVICE FOR DETECTING A FLAW IN A COMPONENT

CROSS-REFERENCE TO RELATED APPLICATIONS

This application claims the benefit of U.S. Provisional Application No. 61/109,345, filed Oct. 29, 2008, the entire disclosure of which is herein incorporated by reference.

FIELD OF THE INVENTION

The invention relates to a device for detecting a flaw in a component, in particular delamination in a bearing region of a hole, by means of at least one probe, it being possible to emit and detect an ultrasound field by means of the at least one probe.

Composite materials and in particular carbon-fibre-reinforced thermosetting polymers are increasingly being used in the modern aircraft construction industry. In principle, complete fuselage sections or barrels can be produced in one piece in a winding process, for example by successively applying carbon fibre strands which are pre-impregnated with epoxy resin (prepreg strands) to a rotating winding mandrel. Particular problems are encountered, inter alia, as a result of the large diameter dimensions of fuselage sections for modern passenger aircraft, which require the use of correspondingly large and therefore heavy winding cores. In addition, the surface quality of a fuselage section produced in a winding process is generally unsatisfactory and further costly steps are required to smooth the component surfaces once the winding process itself is complete. Furthermore, fibre-reinforced thermosetting materials exhibit shrinkage during the curing process and these could lead to differences in dimensions which cannot be easily reproduced, so it is often impossible to join fuselage sections produced in one piece by winding in a stress-free manner to form a fuselage airframe without taking additional tolerance compensation measures. Aside from the above considerations, large wound CFRP components also require curing devices of appropriate dimensions. Finally, if they are damaged, single-piece wound fuselage sections are very costly to repair, if they can even be repaired at all, since it is necessary in some circumstances to replace an entire fuselage section within the aircraft fuselage airframe, and this represents a total economic write-off.

A major advantage of wound fuselage sections in comparison with the conventional full-aluminium construction is that they are free of longitudinal seams, thus providing a considerable potential weight reduction, and the known problems of corrosion and fatigue encountered as a result of the conventionally required connection members are therefore eliminated, which means that fuselage sections of this type achieve longer life cycles in comparison to the conventional full-aluminium construction. However, it should be noted in this respect that the cost of producing transverse seams is considerably higher than that of longitudinal seams.

An alternative to producing fuselage sections by winding is assembling fuselage sections formed from a plurality of prefabricated shell segments. Producing fuselage sections with large diameter dimensions by joining at least two shell segments avoids many of the aforementioned drawbacks. However, the shell construction has the disadvantage that longitudinal seams are required to join the shell segments, thus increasing the weight further, and these seams require a plurality of connection members, which have a detrimental effect on the corrosion-resistance and fatigue-resistance of the entire fuselage section. If the shell segments along the longitudinal seams are not joined solely by adhesive connections, the production of longitudinal seams requires that a large number of holes be formed for the connection members required. However, the holes generally weaken the CFRP materials used structurally and may cause further structurally relevant flaws such as delamination, in particular in the region of the internal hole surface.

A plurality of methods and devices for non-destructive material testing with ultrasound which can be employed to examine metal and non-metal materials of all types are known from the prior art. When testing metal plates and sheets and CFRP shells with ultrasound, the ultrasound employed is generally introduced into the surface of the tool/component to be tested in a perpendicular direction.

However, when the applicant carried out a plurality of practical tests on drilled CFRP components, it was found that the known devices and methods were unsuitable for investigating holes in CFRP components since it is not possible to achieve a reliable level of resolution or to determine the position of small flaws in the material, in particular delamination in the bearing region.

SUMMARY OF THE INVENTION

It is therefore the object of the invention to provide a device with which flaws in particular in the bearing region of holes in composite materials can be reliably detected.

This object is achieved by a device having the features of claim 1.

Delamination in the bearing region of holes can now be detected with a previously unattainable degree of resolution on account of the fact that the ultrasound field interacts with the component at an angle of incidence $\alpha$ of greater than 0° from a normal of a component upper side.

In contrast with the above, the conventional perpendicular alignment of the probe, and thus the sound beam emitted by the probe, means that the majority of the sound energy is directed through the hole without interaction taking place, so this portion of the sound energy makes an insufficient contribution to flaw detection, and disruptive signal portions originating from the hole wall have a negative effect on the assessment of flaws.

The high resolution of the device according to the invention makes it possible to detect not only the presence of delamination, even small areas of delamination, but also the exact spatial location thereof in the bearing area of a hole. In order to detect flaws reliably, it is generally necessary to position a medium between the probe and the composite component, the impedance and geometry of said medium being such that the sound transmission and the desired acoustic radiation direction in the test object are ensured, i.e. undesirable reflection and scattering effects are also prevented. The coupling element or the transmission element is generally what is known as a "stand-off" in the form of a plastics material member wetted with coupling liquid or a water tank or a volume of water comprising a resilient membrane arranged on the lower side thereof to ensure that the probe can be moved relative to the component.

An advantageous embodiment of the device is provided with an evaluation unit, wherein a surface echo, an intermediate echo, a back-wall edge echo or any combination of these echoes of the ultrasound field emitted by the probe is evaluable by means of the evaluation unit to indicate the presence of the flaw.

Depending on its construction and the device, the probe or linear probe can emit ultrasound fields in a frequency range of between 1 and 30 MHz and can simultaneously detect reflected ultrasound signals caused by interaction with the component using measurement methods, that is to say the probe functions both as a transmitter and as a receiver in a time-shifted manner. In principle, the probe may have a separate transmitter and receiver. The source of ultrasound in the probe is piezoelectric elements or electroacoustic actuators which are able to transform an externally applied voltage into mechanical movement, largely without delay and in a proportional manner, and conversely, can convert mechanical deformations in the piezoelements caused by ultrasound waves impinging on the probe into a voltage once again.

The A-scope displays produced by the probe at a particular component position from electrical measured values of the piezoelectric elements are digitised in the evaluation unit by fast analogue-digital converters and are processed in a specific computer unit in real-time in such a way that is possible to produce a visual graphic display. The position of the probe during the hole inspection process is advantageously specified in polar coordinates r, $\phi$. The radius r corresponds to the distance of the probe from the longitudinal axis of the hole or the centre of the hole, whereas the angle $\phi$ corresponds to the angle of rotation, in degrees, of the probe in its respective measurement position about the longitudinal axis of the hole.

In what are known as A-scope displays, the measured signals are shown graphically against the travel time or component depth.

This makes it possible to display the intermediate echo amplitudes, back-wall edge echo amplitudes and/or intermediate echo travel times (i.e. intermediate echo depths) measured by the probe as what are known as "B-scope displays" or "C-scope displays" on a monitor. "B-scope displays" are, to all intents and purposes, cross-sectional displays of the composite components tested, whereas "C-scope displays" are plan-view-like, planar, colour-coded displays of the component.

In a further advantageous embodiment, it is provided that the presence of the flaw is signalable optically and/or acoustically by an output means.

The data from the ultrasound probe or the ultrasound linear probe processed in the evaluation unit are preferably displayed for ease of evaluation on a large, colour-capable screen to produce a display which is in colour, and is therefore clear, of the ultrasound echo, which, in the case of B-scope displays, exhibits some similarity to the component geometry, detected by the probe.

In an advantageous embodiment, the ultrasound field is emitted from the at least one probe in a pulsed manner with a pulse frequency of up to 20 kHz and a pulse length of less than 10 $\mu$s.

Since the ultrasound is emitted for short periods of time at a pulse frequency of up to 20 kHz, only short ultrasound pulses or wave packets of the wave group with a pulse length of less than 10 $\mu$s are emitted.

The main frequency of these ultrasound pulses is largely determined by the vibration characteristics of the vibrator element of the probe, but is also a function of the ultrasound device (excitation, filter) and the sound characteristics of the material to be tested.

The pulse repetition frequency, ultrasound test frequency and ultrasound pulse length are selected in such a way that any return ultrasound pulse packets, originating from material flaws, over a sufficiently long interference-free path in the material to be tested can be sufficiently time resolved.

In a further advantageous embodiment, it is provided that a coupling element, in particular a stand-off wedge, is arranged between the at least one probe and the upper side of the component, wherein an angle of incidence $\alpha$ between the ultrasound field and the normal of the upper side of the component is greater than 0°.

The stand-off wedge is generally produced from plastics material. It is acoustically coupled to both the active vibrator surface of the probe and the component surface to minimise transmission loss. A stand-off wedge is generally formed with a water film or with a special coupling paste. This means that the relevant main component of the sound field is radiated into the bearing region in question at an angle of up to 20° from a normal of the upper side of the component and it is possible to achieve particularly high spatial resolution with a high useful signal to noise ratio.

In a further embodiment of the invention, the probe or linear probe is moveable relative to the hole in at least two spatial directions by a positioning unit.

In this case, it is particularly suitable to move the at least one probe using polar coordinates with a radius r and an angle of rotation $\phi$ from the hole axis. In this case, the radius r is equal to the distance of the probe from the longitudinal axis of the hole. It is alternatively possible to use Cartesian coordinates, in which the position of the at least one probe is detected parallel to the x-axis, y-axis and z-axis.

The angle of rotation $\phi$ or the radius r or the Cartesian xyz-coordinates can be determined for example using optical rotary encoders, digital displacement measurement means or other distance detection methods. In order to achieve the high mechanical resolution and reproducibility generally required for sufficient accuracy, the positioning means is equipped for example with play-free spindle drives which are driven by motors with toothed gear or toothed belt mechanisms connected downstream.

An advantageous development of the device according to the invention provides that the at least one probe is a linear probe comprising a plurality of individual vibrator elements which are in particular arranged behind one another in a row and are activatable individually, wherein each ultrasound field emitted by an individual vibrator element is emitted at an angle of incidence $\beta$ of 0° from the normal of the upper side of the component and wherein the linear probe being aligned approximately horizontally relative to the upper side of the component.

It is also advantageously possible to focus the sound field at a particular depth for the respective active group of individual vibrator elements.

Using the linear probe in the device has the particular advantage that radial movement is not achieved by mechanical movement but by activating the individual vibrator elements electronically and successively in groups of 1 to 8, 2 to 9, 3 to 10, etc for example. In this example activation sequence, each group comprises eight active vibrators, i.e. piezoelectric acoustic converters. However, the linear probe must be secured at a suitable fixed distance from the centre of the hole. In this way, it is possible for the linear probe to test the bearing region of primary interest with a simple rotational movement about an angle $\phi$ or to carry out the test in one go with a linear movement. This reduces the constructional costs in particular for the positioning means required to guide the probe above the composite component since said positioning means need only now be moved along at least one axis. Since a longitudinal axis of the linear probe is generally arranged transverse to the direction of movement of the positioning means, it is generally no longer necessary to be able to move the positioning means parallel to the y-axis.

In principle, the device may also be equipped with at least one matrix probe or matrix array, as they are known, which extends the "one-dimensional" linear probe by another spatial dimension. However, a matrix probe of this type would have to be manufactured specifically and take into account the geometry of the bearing region to be tested. For example, the individual vibrator elements would have to be arranged in the form of ring segments, the rings being nested within one another in a concentric manner. With a circular matrix ultrasound probe of this type, it would be possible to scan a portion of an upper side of a composite part to be tested and/or a region around a hole in the component in a single step, it only being necessary to position the probe once.

In a further advantageous development, it is provided that superposing the ultrasound emitted by each of the individual vibrator elements forms a superposed ultrasound field.

The ultrasound fields emitted from each of the aforementioned elements in the linear probe are superposed in accordance with the principles of general wave theory to form a resulting obliquely-radiating superposed ultrasound field.

A further advantageous development of the invention provides that the individual vibrator elements in the linear probe re activatable, in particular by a phase activation means, in such a way that an angle of incidence $\alpha$ between the resulting superposed ultrasound field and the normal of the upper side of the component is greater than 0°.

In this way, the same effect of radiation oblique to the normal, as achieved by a single ultrasound probe with a stand-off wedge arranged beneath it, is also achieved with a linear ultrasound probe. However, in contrast to the mechanical arrangement using a stand-off wedge, oblique radiation is achieved in this case by using electronic means.

By activating the linear probe with an electronic phase activation means, which is generally an integral component of the ultrasound evaluation unit within the device, it is also possible to adapt the superposed ultrasound field emitted easily by changing suitable parameters in the evaluation unit, such as the chronological activation order of the individual vibration elements in the linear probe by an electronic activation means, to the respective requirements during the test.

In conventional linear probes, 32, 64, 96 or 128 individual vibrator elements are usually combined to form a unit. The individual vibrator elements in the linear probe are generally activated in groups, each adjacent group typically being activated successively in a time-shifted manner. Superposed ultrasound fields of widely variable geometries and in particular with a main beam inclined relative to a normal of the upper side of the component for oblique radiation can be generated by correspondingly adjusting the parameters of the activation unit in the ultrasound evaluation unit by way of a software menu.

Further advantageous embodiments of the device are set out in the other claims.

BRIEF DESCRIPTION OF THE DRAWINGS

In the drawings.

In the drawings, like constructional elements are denoted with like reference numerals.

DESCRIPTION OF EXEMPLARY EMBODIMENTS

Figure 1:
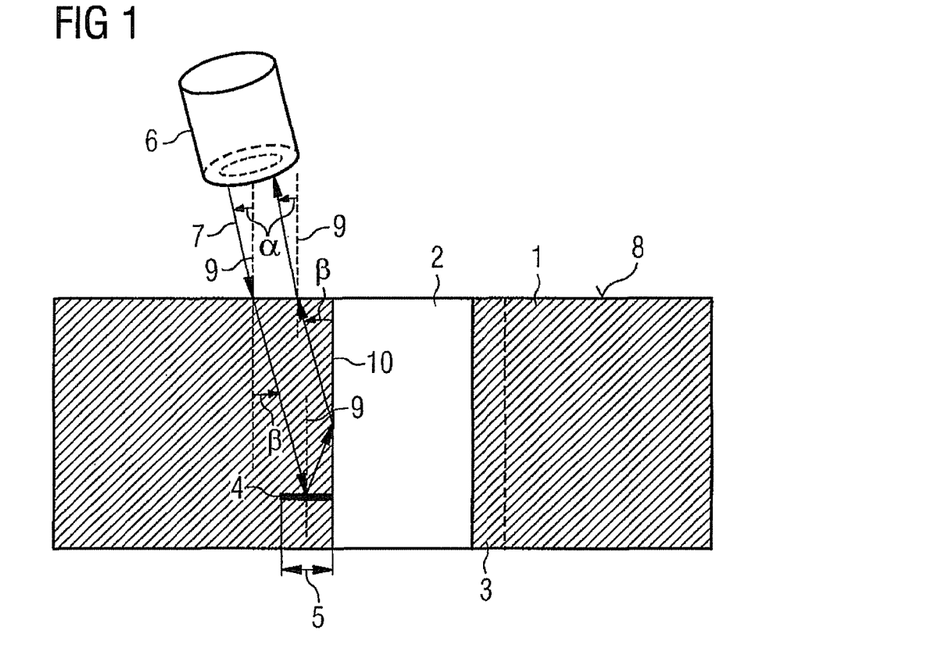
FIG. 1 is a schematic diagram of the operation of the device.

FIG. 1 is a schematic view of the operation of a device formed according to the invention.

A cylindrical hole 2 is formed in a component 1. The component 1 is preferably any composite component generally formed from a carbon-fibre-reinforced epoxy resin. There is delamination 4 to be detected having a width 5 in a bearing region 3 of the hole 2. The term "delamination" refers to a region in which reinforcing fibre layers have become detached or separated from the surrounding polymer matrix. These air-filled delamination regions may be formed during the process of manufacturing the component 1 or when the holes are formed. In both cases, the mechanical loading capacity of a connection between the component 1 and an attachment, formed for example by introducing bolts or rivets into the hole 1, is detrimentally affected, so therefore delamination in the region of holes in composite components must be able to be reliably detected in a continuous test process.

Ultrasound 7 is emitted by the probe 6 in the direction of an upper side 8 of a component. Despite the simplified illustration in FIG. 1, the ultrasound 7 is not a concentrated beam with a normal negligible degree of divergence like a laser beam, and but is rather a plurality of drop-shaped sound radiation lobes of different lengths and sound pressures emitted from the probe. The ultrasound 7 is emitted and radiated into the component 1 according to the invention at an angle $\alpha$, which is greater than 0°, from a normal 9 of the upper side 8 of the component. A value of up to 20° is selected for the angle $\alpha$ for optimal results. A coupling element, not shown in FIG. 1 for the sake of clarity, is positioned between the probe 6 and the upper side 8 of the component in order to minimise reflections caused by the phase transition in the region of the upper side 8 of the component (cf. FIG. 2). This coupling element may be formed for example by a water stand-off. It is also possible to use a suitable plastics material wedge, the upper side of which is acoustically connected to the ultrasound vibrator by a film of coupling paste or coupling liquid and the lower side of which is similarly equipped in order to transmit the ultrasound into the component and to achieve a smooth sliding movement.

Within the component 1, the ultrasound 7 extends in a straight line at an angle $\beta$ which is also greater than 0°, then impinges on the delamination 4 of width 5 and is strongly reflected thereby, subsequently impinges on an internal surface 10 of the hole 2 and is strongly reflected thereby, again at an angle $\beta$, then emerges from the upper side 8 of the component again at the angle $\alpha$ and finally impinges on the probe 6 again. The relationship of the two angles $\alpha$ and $\beta$ is given by the relation $$\frac{\sin\alpha}{\cos\beta} = \frac{c_1}{c_2},$$

where $c_{1,2}$ represents the propagation speed of the ultrasound 7 in the respective medium (air or composite material of the component). The measurement signal generated by the probe 6 is amplified, filtered, digitised, stored and mathematically processed in an evaluation unit (not shown). In an output means connected downstream, the processed measurement signal is represented acoustically and/or optically.

Owing to the fact that the ultrasound 7 is radiated obliquely according to the invention into the component 1, the reflection of the ultrasound 7 in the region of the delamination 4 is amplified by a corner reflector-type effect with an increasing active area in such a way that it is possible to resolve ultrasound measurements in the bearing regions of holes in composite components to a higher degree using the device. This also advantageously prevents disruptive signals on account of the grazing incidence on the hole surface. In this way, delamination can be detected more reliably and the position thereof determined more accurately. In particular, this prevents the majority of the ultrasound 7 emitted by the probe 6 being lost without interaction through the hole 2, and thus lost for use in evaluation, when the ultrasound 7 is radiated in the region of the hole 2.

Figure 2:
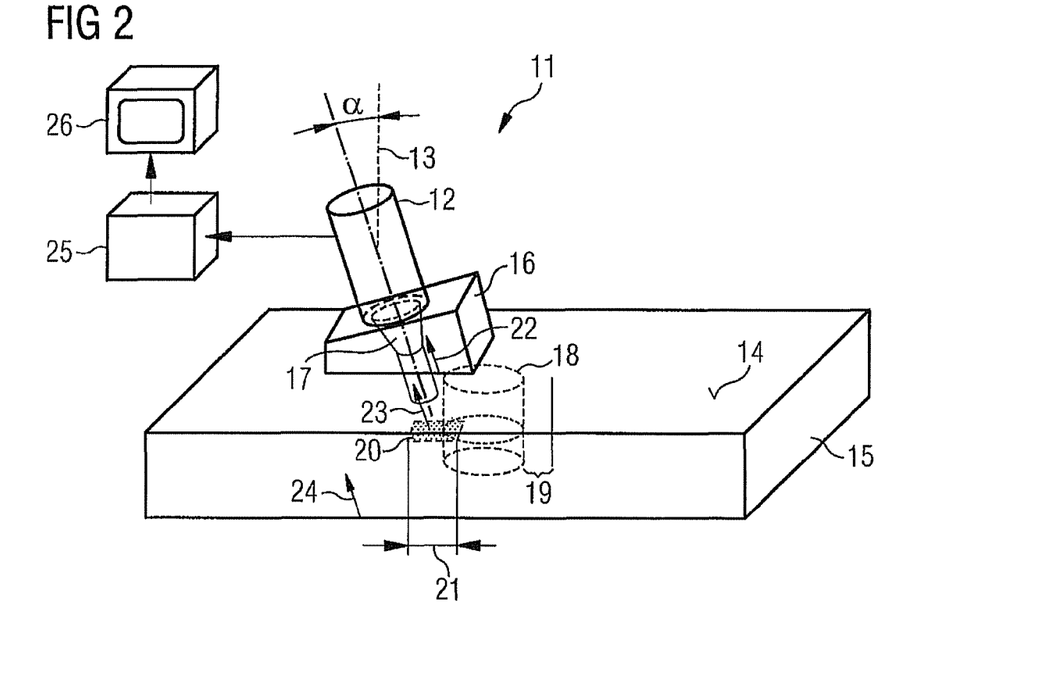
FIG. 2 is an embodiment of the device comprising a single probe using a stand-off wedge.

FIG. 2 shows a first embodiment of the device.

A device 11 comprises, inter alia, a probe 12 which is cylindrical for example and is arranged at an angle $\alpha$ of between 5° and 25° from a normal 13 of an upper side 14 of a component 15 to be tested. A stand-off wedge 16 for obtaining optimal coupling of the lobe-shaped ultrasound field 17 emitted by the probe 12 is positioned between the probe 12 and the upper side 14 of the component. A hole 18, with a delamination 20 of a width 21 in the bearing region 19 thereof, is formed in the component 15. A surface echo 22, an intermediate echo 23 and a back-wall edge echo 24 are produced by the ultrasound field 17. The echoes 22 to 24 are appropriately evaluated in a complex evaluation unit 25 and are displayed on an output means 26 which is generally a colour LCD monitor. Since the ultrasound 17 is radiated obliquely according to the invention at an angle of inclination $\alpha$, a stronger intermediate echo 23 is produced by the delamination 20, thus enabling the device 11 to achieve a significantly higher degree of resolution with regard to the presence and position of the delamination 20.

Figure 3:
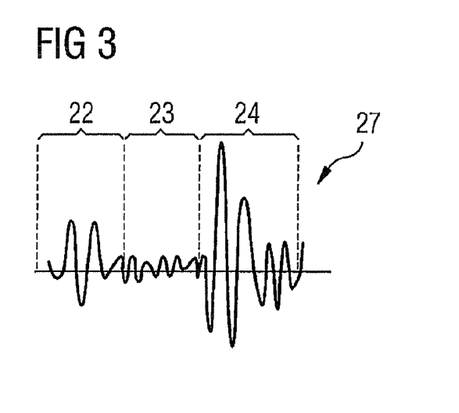
FIGS. 3, 4 show an example of the measurement results, in particular A-scope displays, obtained by the device.
Figure 4:
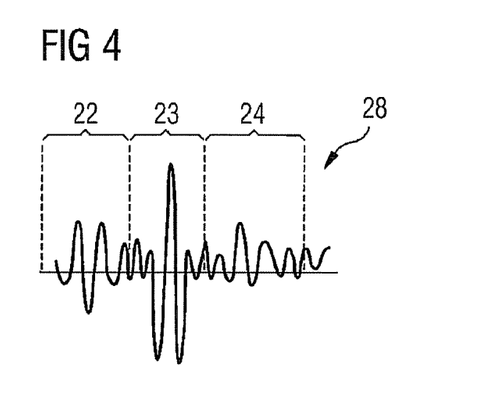

FIGS. 3 and 4, which will be discussed simultaneously in the description below, show examples of the curves of two A-scope displays produced with the device according to FIG. 2.

In the upper A-scope display 27, which shows an ultrasound signal against time or component depth, there is no delamination present or displayed, whereas delamination is displayed by an intermediate signal in the lower A-scope display 28.

In addition to the relatively weak surface echo 22, the A-scope display 27 shows a marked back-wall edge echo 24, whereas there is no intermediate echo 23 apart from low noise signals. This leads one to conclude that there is no delamination in the region of the hole. The A-scope display 28 is quite different, since, in comparison with the first A-scope display 27, there is a marked intermediate echo 23 and the back-wall edge echo 24 is considerably less pronounced in the lower A-scope display 28 compared with the upper A-scope display 27.

Figure 5:
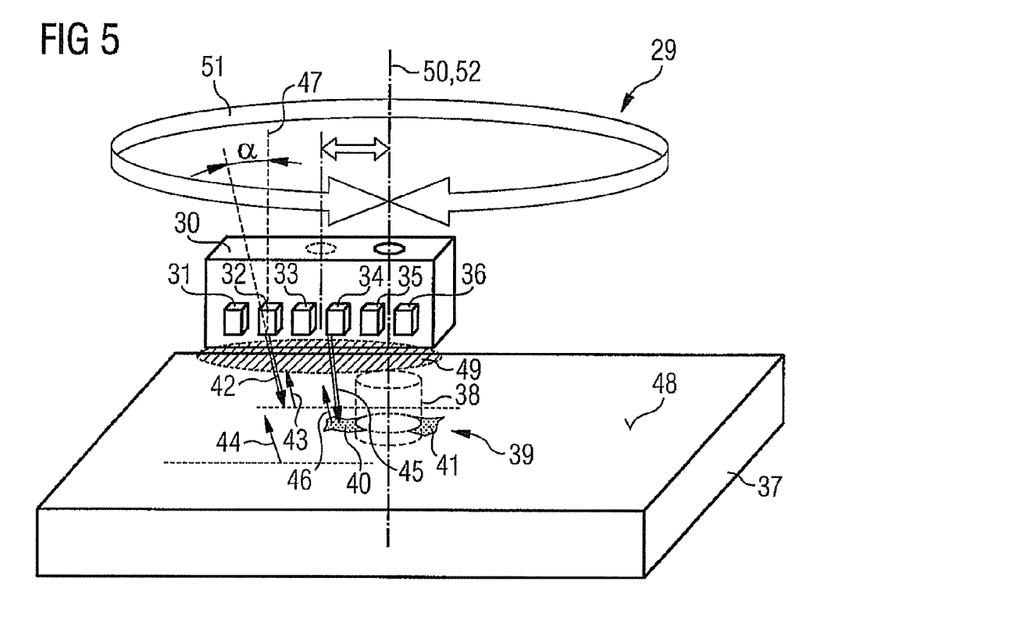
FIG. 5 is a variant embodiment comprising a linear probe which can be positioned in the region of the hole and the linear axis of which passes through the centre of the hole.
Figure 6:
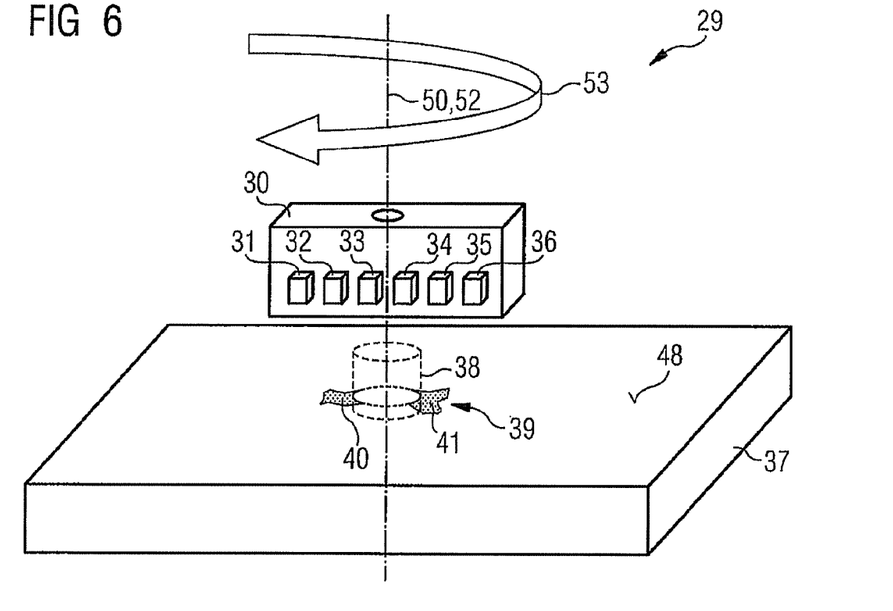
FIG. 6 is a variant embodiment comprising a linear probe which can be positioned in the region of the hole.

FIGS. 5 and 6 show the basic structure of a second and third variant embodiment of the device which are provided with what is known as a linear probe, in contrast to the first variant embodiment.

A device 29 comprises, inter alia, a linear probe 30 equipped in the example shown in FIG. 5 with a total of six individual vibrator elements 31 to 36. Within the housing of the linear probe 30, the individual vibrator elements 31 to 36 are spaced at an equal distance from one another and are arranged behind one another in a line. The construction and function of the individual probes 31 to 36 combined in the linear probe 30, when viewed individually, correspond to the construction and function of the ultrasound probes 6, 12 explained above in relation to FIGS. 1 and 2. The individual vibrator elements 31 to 36 integrated in the linear probe 30 are able to emit ultrasound on the one hand and receive ultrasound on the other hand in such a way that said received ultrasound can be evaluated by the ultrasound evaluation unit. Positioned beneath the linear probe 30 is a component 37 which is to be tested and has a cylindrical hole 38 with two delamination regions 40, 41 in the bearing region 39 thereof.

The ultrasound field 42 emitted by the individual vibrator element 32 produces a weak surface echo 43 and a back-wall edge echo 44, whereas an ultrasound field 45 radiated by the individual vibrator element 34 is reflected at least in part in the interior of the component 37 by the delamination 14 and produces an intermediate echo 46 which represents a clear indication of a flaw in the component 37. In contrast to the single probe, the individual vibrator elements 31 to 36 of the linear probe 30 each emit the ultrasound field 42, 45 at an angle of 0° from a normal 47 of the upper side 48 of the component or of the linear probe 30. The incline according to the invention of the ultrasound field 42, 45 of between 0° and 30° is produced by activating the individual vibrator elements 31 to 36 within the linear probe 30 in a suitable manner, in particular a time-shifted manner, in groups. In this way, the individual ultrasound wave fields of the individual vibrator elements 31 to 36 are superposed in accordance with the laws of general wave theory to form a superposed ultrasound field 49, the crucial active main component of which has the desired angle of incidence of between 0° and approximately 20° from the upper side 48 of the component.

By rotating the linear probe 30 by 360° about a hole axis 50, as indicated by the arrow 51, the entire bearing region 39 can be tested for the presence and/or position of the delamination regions 40, 41. In this case, the linear probe 13 rotates about the hole axis 50, i.e. the axis of rotation 52 of the linear probe 30 extends horizontally and is offset, as indicated by the white, horizontal double-headed arrow, parallel to the hole axis 50.

In contrast to the variant shown in FIG. 5, the linear probe 30 comprising the individual vibrator elements 31 to 36 is arranged centrally above the hole 38 in the component 37 in the third variant of the device 29 shown in FIG. 6, i.e. the hole axis 50 coincides with the axis of rotation 52 of the linear probe 30, with the particular advantage that, for a complete test of the bearing region 39 of the hole 38, is it is only necessary to rotate the linear probe 30 by 180° about the axis of rotation 52 to scan the bearing region 39 completely, as illustrated by the arrow 53. In this way, the testing time required can be halved using the third variant of the device 29 according to the invention.

In order to achieve a high, uniform degree of coupling, a stand-off (not shown), in particular a water-filled stand-off or "water stand-off", is positioned between the linear probe 30 and the upper side 48 of the component (cf. FIG. 2). The linear probe 30 is rotated manually or by a positioning means (also not shown) controlled by the evaluation unit.

Figure 7:
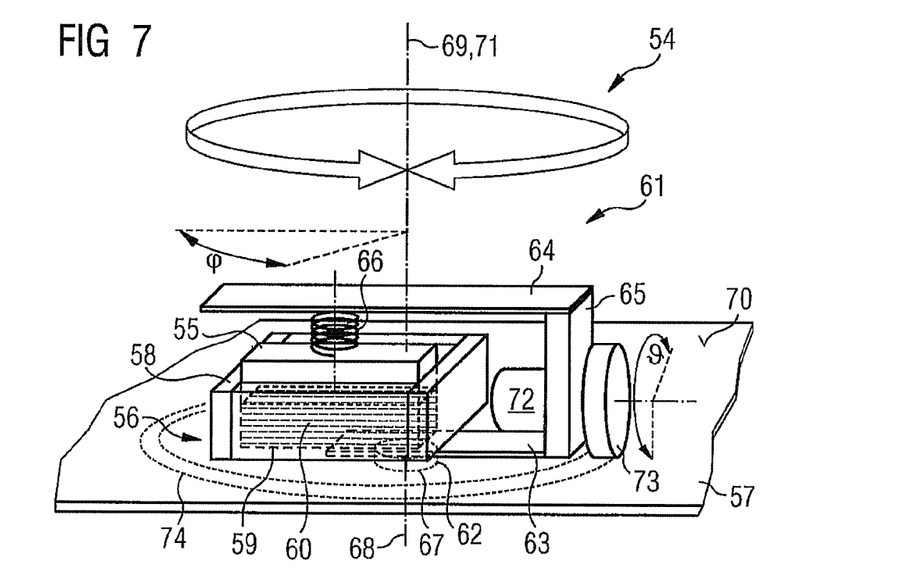
FIG. 7 is an embodiment of an automatically operating device according to FIG. 6.

FIG. 7 shows a possible technical rearrangement of the second variant.

A device 54 comprises, inter alia, a linear probe 55 which is vertically received in a resilient manner in a water stand-off 56 as a coupling element to achieve largely loss-free ultrasound transmission. The linear probe 55 is fitted into the water stand-off 56 in such a way that no water escapes therefrom when the linear probe 55 is moved vertically. Sealing members may have to be provided between the linear probe 55 and the walls of the stand-off 56 for this purpose. The water stand-off 56 enables the ultrasound emitted by the linear probe 55 to be coupled in a virtually loss-free manner to a component 57 to be tested and allows the ultrasound reflected by the component 57 to be returned to be linear probe 55 with a low degree of loss.

The water stand-off 56 is formed by a cuboidal container 58, the lower side of which is sealed in a water-tight manner by a resilient membrane 59 of low thickness and which is ideally filled completely with clean water 60 without bubbles. The linear probe 55 is spatially positioned relative to a hole 62 formed in the component 57 by a U-shaped holder 61 as a positioning means controlled by a control and operating means (not shown). For this purpose, the water stand-off 56 is fastened to an inner face of a lower leg 63 of the U-shaped holder 61. An upper leg 64 is formed so as to be resilient and is connected to the lower leg 63 by a vertical web 65. A compression spring 66 is arranged between the upper leg 64 and the linear probe 55 to support the resilient effect. The lower side of the lower leg 63 has a pin 67 which can be inserted into the hole 62 with a positive fit at least in regions. In this way, the holder 61, together with the linear probe 55, can be rotated by any desired angle $\phi$ about a hole axis 68 which also represents a normal 69 of an upper side 70 of the component and an axis of rotation 71 of the entire device 54.

A motor 72 which can drive a wheel 73 is provided to ensure that the testing process can be carried out fully automatically. In this case, the wheel 73 rolls on an annular roll path 74 on the upper side 70 of the component. It is possible to detect an angle of rotation $\theta$ using a rotary encoder (not shown) and use said angle for subsequent digital graphical processing.

In the description below, reference is made simultaneously to FIGS. 8 to 11 which show graphical representations of measurement results which were obtained for example using a linear probe according to FIG. 7, graphically processed in an evaluation unit connected downstream and displayed.

Figure 8:
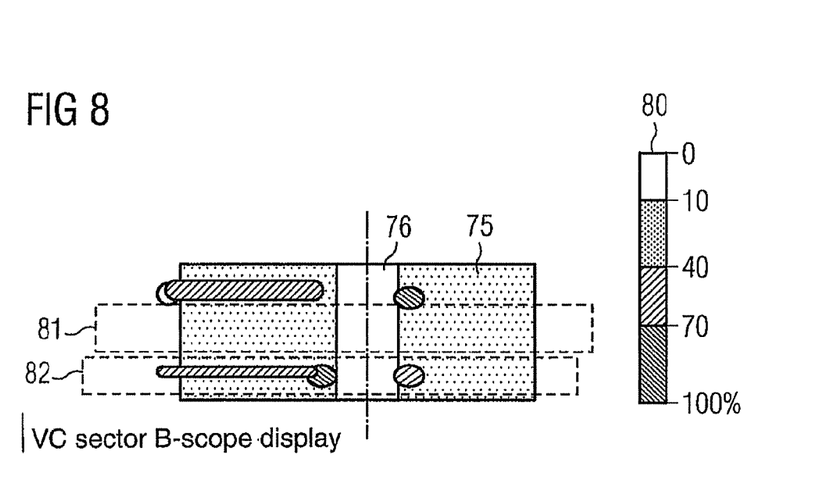
FIG. 8 is a VC sector B-scope display with a flaw-free hole.
Figure 10:
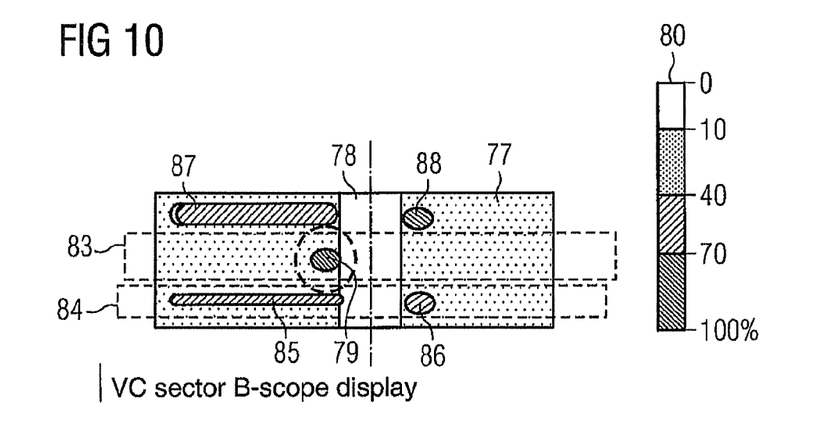
FIG. 10 is a VC sector B-scope display of a component with a defective hole.

FIG. 8 shows what is known as a VC sector B-scope display of a component 75 with a flaw-free hole 76, i.e. in particular without delaminations, whereas FIG. 10 shows a VC sector B-scope display of a defective component 77 with a flaw-containing hole 78 which comprises a delamination 79 in the boundary area. The abbreviation "VC" stands for "volume corrected", i.e. this is a sector display which has been volume-corrected by numerical processes or algorithms.

Figure 9:
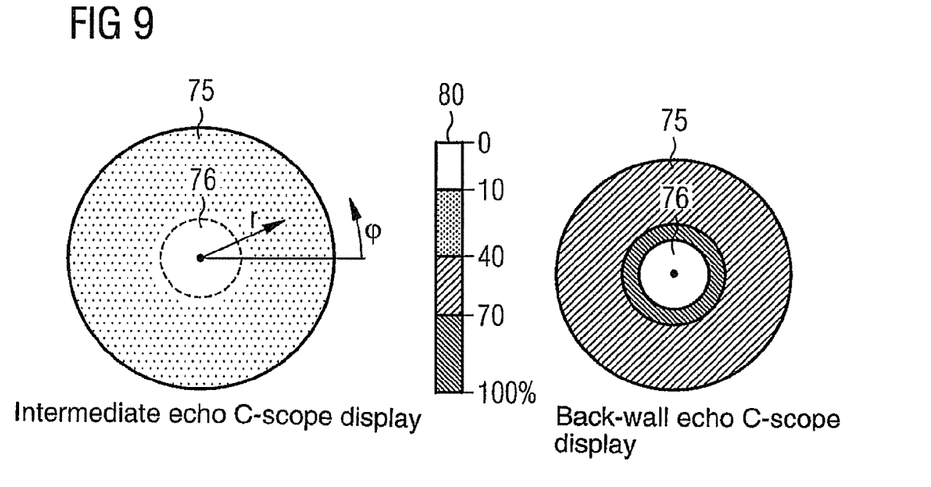
FIG. 9 is an intermediate echo C-scope display and a back-wall echo C-scope display of the component of FIG. 8.

The left-hand side of FIG. 9 shows an intermediate echo C-scope display of the hole 76, and the right-hand side of FIG. 9 illustrates a back-wall echo C-scope display of said hole.

Figure 11:
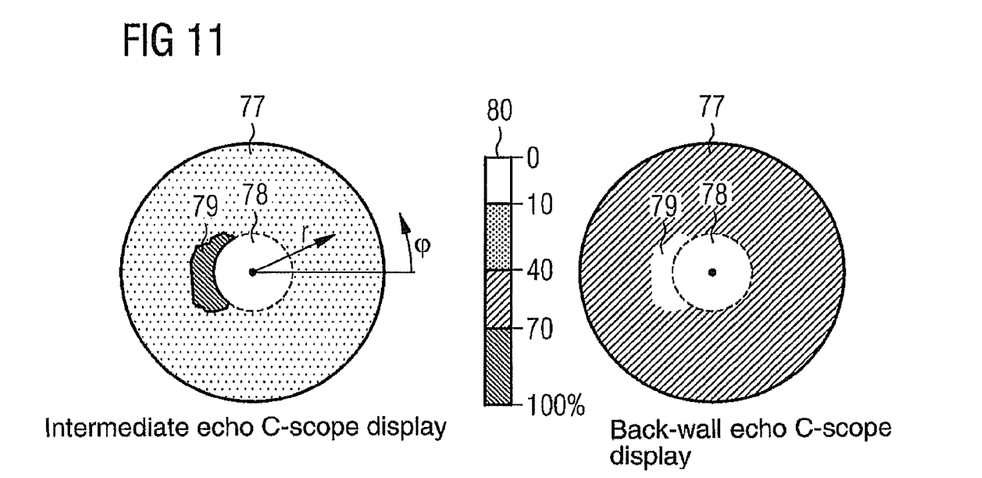
FIG. 11 is an intermediate echo C-scope display and a back-wall echo C-scope display of the component in FIG. 10.

Correspondingly, the left-hand side of FIG. 11 shows an intermediate echo C-scope display of the defective hole 78 and the right-hand side shows a back-wall echo C-scope display of this hole. The delamination 79 can be seen clearly in both diagrams.

The polar coordinates r, $\phi$ represent a radius r, i.e. a distance between an example measuring point observed in FIGS. 9 and 11 and a longitudinal axis of the tested hole, and the angle of rotation $\phi$ at which the measurement is carried out. The individual measurement points can be plotted successively with the linear probe 55 of the device according to FIG. 7.

The grey shading in each of FIGS. 8 to 11 each correspond to the grey shading of a reference scale 80 and the percentage values associated there with. The percentage values or intervals of 0% 10%, 10% to 40%, 40% to 70% and 70% to 100% associated with the grey shading represent the maximum screen height (SH, amplitudes) achieved or displayed in each case for each ultrasound echo and obtained in the intermediate echo gates 81 and 83 framed in each case by broken lines and in the back-wall echo gates 82, 84, also framed in broken lines, and in the other regions of the components 75, 77, including the holes 76, 78. These screen heights are processed and displayed on the display unit (screen) (not shown) of an evaluation unit for a user to enable flaws, in particular delamination, to be detected more easily.

For example, the diagram according to FIG. 10 indicates a screen height of between 70% and 100% (cf. reference scale 80) in the region of the delamination 79, whereas the echoes in the rest of the intermediate echo gate 83 of the component 77 only reach a screen height of between 10% and 40%. In the region of the back-wall echo gate 84, echo screen heights of between 10% and 40% are produced and SH values of from 40% to 70% are achieved in each of the spatially delimited zones 85 (oval) and 86 (slightly elliptical). Two further locally delimited zones 87, 88 are located above the intermediate echo gate 83. In the elongate oval zone 87 on the left-hand side, the SH values are between 40% and 70%, whereas the slightly elliptical zone 88 on the right-hand side exhibits SH values of between 70% and 100%. However, in the regions of the component 77 surrounding the two zones 87 and 88 (above the intermediate wall echo gate 84) the SH values are considerably lower and only reach values of between 10% and 40% so it is possible to detect the delamination 79 clearly. FIG. 8 shows that the component 75 also has five elongate, oval and circular or slightly elliptical zones with different SH values, which have not been provided with reference numerals for greater clarity.

In this way, the screen heights of all the measured echoes from the components 75, 77 according to FIGS. 8, 9 and 11 can be quantified.

It is crucial that the diagrams in FIGS. 9 and 11 are what are known as C-scope displays in which the measured ultrasound amplitudes of both the intermediate echo and the back-wall edge echo are shown two-dimensionally in shades of grey or different colours for greater clarity.

By using the device which radiates ultrasound obliquely according to the invention, it is now possible for the first time to detect the presence and position of delamination in a whole region of CFRP composite components in particular with a high degree of resolution and a corresponding good level of accuracy. In addition, the device operates completely automatically and enables short test times to be achieved with reliable detection of flaws.

LIST OF REFERENCE NUMERALS

| | |
|---|---|
| 1 | component |
| 2 | hole |
| 3 | bearing region |
| 4 | delamination |
| 5 | width |
| 6 | probe |
| 7 | ultrasound field |
| 8 | upper side of component |
| 9 | normal |
| 10 | internal hole surface |
| 11 | device |
| 12 | probe |
| 13 | normal (upper side of component) |
| 14 | upper side of component |
| 15 | component |
| 16 | stand-off wedge |
| 17 | ultrasound field |
| 18 | hole |
| 19 | bearing region |
| 20 | delamination |
| 21 | width |
| 22 | surface echo |

-continued

LIST OF REFERENCE NUMERALS

| | |
|---|---|
| 23 | intermediate echo |
| 24 | back-wall edge echo |
| 25 | evaluation unit |
| 26 | output means |
| 27 | A-scope display |
| 28 | A-scope display |
| 29 | device |
| 30 | linear probe |
| 31 | individual vibrator element |
| 32 | individual vibrator element |
| 33 | individual vibrator element |
| 34 | individual vibrator element |
| 35 | individual vibrator element |
| 36 | individual vibrator element |
| 37 | component |
| 38 | cylindrical hole |
| 39 | bearing region |
| 40 | delamination |
| 41 | delamination |
| 42 | ultrasound field (radiation lobe) |
| 43 | surface echo |
| 44 | back-wall echo |
| 45 | ultrasound field (radiation lobe) |
| 46 | intermediate echo |
| 47 | normal (upper side of component) |
| 48 | upper side of component |
| 49 | superposed ultrasound field |
| 50 | hole axis |
| 51 | arrow (rotation arrow 360°) |
| 52 | axis of rotation (linear probe) |
| 53 | arrow (rotation arrow 180°) |
| 54 | device |
| 55 | linear probe |
| 56 | water stand-off |
| 57 | component (for example composite component) |
| 58 | cuboidal container |
| 59 | membrane |
| 60 | water |
| 61 | U-shaped holder |
| 62 | hole |
| 63 | lower leg |
| 64 | upper leg |
| 65 | web |
| 66 | spring |
| 67 | pin |
| 68 | hole axis |
| 69 | normal |
| 70 | upper side of component |
| 71 | axis of rotation (device) |
| 72 | motor |
| 73 | wheel |
| 74 | roll path (wheel) |
| 75 | component |
| 76 | hole |
| 77 | component |
| 78 | hole |
| 79 | delamination |
| 80 | reference scale |
| 81 | intermediate echo gate |
| 82 | back-wall echo gate |
| 83 | intermediate echo gate |
| 84 | back-wall echo gate |
| 85 | zone |
| 86 | zone |
| 87 | zone |
| 88 | zone |

Items 30–36 are bracketed together as "linear probe".

The invention claimed is:

1. Device for detecting a delamination in a bearing region of a hole, by means of at least one probe, wherein an ultrasound field is emittable and detectable by means of the at least one probe, wherein the ultrasound field interacts with the component at an angle of incidence α of greater than 0° from a normal of an upper side of the component, wherein the at least one probe is a linear probe comprising a plurality of individual vibrator elements, wherein each ultrasound field emitted by an individual vibrator element is emitted at an angle of incidence β of 0° from the normal of the upper side of the component and the linear probe is aligned approximately horizontally relative to the upper side of the component, wherein the individual vibrator elements in the linear probe are activatable in such a way, that the angle of incidence α between the superposed ultrasound field and the normal of the upper side of the component is greater than 0°, wherein the linear probe is arranged centrally or offset relative to the hole by a holder, and wherein the linear probe is rotatable receivable in the hole by means of the holder and a pin.

2. The device according to claim 1, wherein an evaluation unit is provided, and wherein a surface echo, an intermediate echo, a back-wall edge echo or any combination of these echoes of the ultrasound field emitted by the probe is evaluable by means of the evaluation unit to indicate the presence of the flaw.

3. The device according to claim 1, wherein the presence of the flaw is signalable optically and/or acoustically by an output means.

4. The device according to claim 1, wherein the ultrasound field is emitted from the at least one probe in a pulsed manner with a pulse frequency of up to 20 kHz and a pulse length of less than 10 µs.

5. The device according to claim 1, wherein a coupling element, in particular a stand-off wedge, is arranged between the at least one probe and the upper side of the component, and wherein an angle of incidence α between the ultrasound field and the normal of the upper side of the component is greater than 0°.

6. The device according to claim 5, wherein the at least one probe is moveable relative to the hole in at least two spatial directions by a positioning unit.

7. The device according to claim 1, wherein superposing the ultrasound field emitted by each of the individual vibrator elements forms a superposed ultrasound field.

8. The device according to claim 1, wherein an angular position α of the linear probe relative to the hole is detectable, in particular by a rotary encoder.

9. The device according to claim 1, wherein the holder, together with the linear probe received therein, is rotatable by a drive unit, in particular a motor.

10. The device according to claim 1, wherein a coupling element, in particular a water stand-off, comprising a container sealed from the upper side of the component by a membrane is arranged between the linear probe and the upper side of the component.

11. The device according to claim 1, wherein the container is filled at least in part with water and the linear probe is arranged above the water.

* * * * *